United States Patent [19]

Takemoto et al.

[11] 4,427,596
[45] Jan. 24, 1984

[54] N-[2-(CYCLOPROPYL) ETHOXY] PHENYLANILIDE DERIVATIVES, AND THEIR PRODUCTION AND USE

[75] Inventors: Ichiki Takemoto, Hyogo; Katsuzo Kamoshita, Osaka; Ryo Yoshida, Kawanishi; Seizo Sumida, Hyogo, all of Japan

[73] Assignee: Sumitomo Chemical Company, Limited, Osaka, Japan

[21] Appl. No.: 243,631

[22] Filed: Mar. 13, 1981

[30] Foreign Application Priority Data

Mar. 27, 1980 [JP] Japan .................................. 55/39753

[51] Int. Cl.³ ........................................ C07C 131/105
[52] U.S. Cl. ................. 260/453 RW; 71/118; 71/120; 564/52; 564/190; 564/203
[58] Field of Search .................... 260/453 RW; 71/120

[56] References Cited

U.S. PATENT DOCUMENTS

| 3,520,674 | 7/1970 | Neighbors | 260/453 RW |
| 3,555,086 | 1/1971 | Weis et al. | 260/453 RW |
| 4,111,683 | 9/1978 | Singer | 260/453 RW |
| 4,123,256 | 10/1978 | Yoshida et al. | 260/453 RW |
| 4,129,436 | 12/1978 | Takemoto et al. | 260/453 RW |
| 4,144,049 | 3/1979 | Yoshida et al. | 260/453 RW |
| 4,149,874 | 4/1979 | Felix | 71/118 |
| 4,260,411 | 4/1981 | Yoshida et al. | 260/453 RW |
| 4,308,213 | 12/1981 | Spatz et al. | 260/453 RW |

FOREIGN PATENT DOCUMENTS 2013669 8/1979 United Kingdom ................... 71/120

*Primary Examiner*—Glennon H. Hollrah
*Attorney, Agent, or Firm*—Birch, Stewart, Kolasch & Birch

[57] ABSTRACT

A compound of the formula:

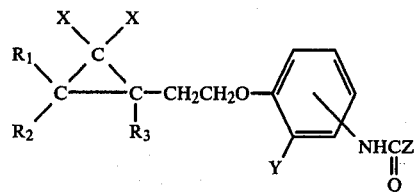

wherein $R_1$, $R_2$ and $R_3$, which may be same or different, are each hydrogen or $C_1$–$C_4$ alkyl, X is chlorine or bromine, Y is hydrogen, chlorine, bromine, fluorine or iodine and Z is N,N-dimethylamino, N-methoxy-N-methylamino, $C_1$–$C_4$ alkyl or $C_3$–$C_6$ cycloalkyl, which is useful as a herbicide.

5 Claims, No Drawings

N-[2-(CYCLOPROPYL) ETHOXY] PHENYLANILIDE DERIVATIVES, AND THEIR PRODUCTION AND USE

The present invention relates to N-[2-(cyclopropyl)ethoxy]phenylanilide derivatives, and their production and use.

The said N-[2-(cyclopropyl)ethoxy]phenylanilide derivatives (hereinafter referred to as "anilide compound(s) (I)") are representable by the formula:

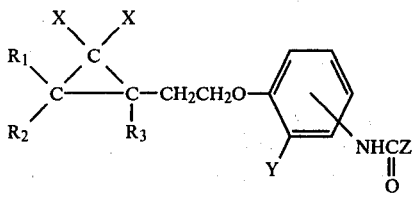

wherein $R_1$, $R_2$ and $R_3$, which may be same or different, are each hydrogen or $C_1$–$C_4$ alkyl, X is chlorine or bromine, Y is hydrogen, chlorine, bromine, fluorine or iodine and Z is N,N-dimethylamino, N-methoxy-N-methylamino, $C_1$–$C_4$ alkyl or $C_3$–$C_6$ cycloalkyl and are useful as herbicides.

Rice plant, wheat, corn, soybean, cotton and sugarbeet and the like are crop plants of world-wide importance and, in the cultivation of these crop plants, chemical control of weeds is necessary to prevent reductions in the yield. Particularly, it is a recent demand that the herbicide to be applied to these crop plants has a selectivity such as a high potency against the weeds while exerting no or lesser damage to the crop plants.

As is well known, urea derivatives exert their herbicidal activity on their inhibitory effect against photosynthesis. Photosynthesis is a physiological function peculiar to higher plants and does not take place in mammals. Accordingly, they can produce a remarkable effect for extermination of higher plants without causing any significant harm to mammals. In fact, herbicidal photosynthesis inhibitors such as N'-4-chlorophenyl-N,N-dimethylurea (monuron) and N'-3,4-dichlorophenyl-N,N-dimethylurea (diuron) are low in mammalian toxicity. Since, however, photosynthesis is common to all of higher plants, the inhibitory effect of urea derivatives is generally shown not only for undesirable plants such as weeds and grasses but also for desirable plants such as crop plants. Thus, they are non-selective and cause frequently serious damages onto crop plants.

It has now been found that the anilide compounds (I), which is a kind of urea derivatives, exert a strong herbicidal activity against a wide variety of weeds and grasses without causing any notable damage onto wheat when applied after emergence. Namely, the application of the anilide compounds (I) to the field of wheat for foliage treatment can exterminate a wide variety of broad-leaved weeds including catchweed bedstraw (*Galium aparine*), redroot pigweed (*Amaranthus retroflexus*), common lambsquarters (*Chenopodium album*), wild mustard (*Brassica arvensis*), common chickweed (*Stellaria media*), black bindweed (*Polygonum convolvulus*) and black nightshade (*Solanum nigrum*) and also control Gramineae grasses such as wild oat (*Avena fatua*) and barnyard grass (*Echinochloa crus-galli*) to a considerable extent with no material toxicity to wheat.

Among the anilide compounds (I), those having a methyl group at the 1-position of the cyclopropane ring such as N'-3-[2-(1-methyl-2,2-dichlorocyclopropyl)ethoxy]phenyl-N-methoxy-N-methylurea (Compound No. 2) and N'-3-[2-(1-methyl-2,2-dibromocyclopropyl)ethoxy]phenyl-N-methoxy-N-methylurea (Compound No. 5) are particularly low in toxicity to wheat and do not produce any damage when applied at a dose of 5 to 10 grams per are. This is a quite advantageous feature.

Besides, the anilide compounds (I) show a remarkable herbicidal potency in paddy fields. Namely, they can exterminate broad-leaved weeds such as pickerel weed (*Monochoria vaginalis*), false pimpernel (*Lindernia pyxidaria*) and toothcup (*Rotala indica*) and also control barnyard grass (*Echinochloa cruss-galli*), slender spikerush (*Eleochoria acicularis*), hotarui (*Scirpus hotarui*), etc. to a significant extent.

The anilide compounds (I) are novel, and of known compounds, N'-3-(2,2-dichlorocyclopropylmethoxy)-phenyl-N,N-dimethylurea (hereinafter referred to as "Control (a)") was described in British Pat. No. 2,013,669 is the most closely related thereto in chemical structure. However, the anilide compounds (I) are much more stronger than the control (a) in herbicidal activity. In addition, the selectivity of the anilide compounds (I) is more excellent than that of the control (a). For instance, the control (a) shows only a weak control against catchweed bedstraw (*Galium aparine*), common chickweed (*Stellaria media*), etc. and its selectivity between these weeds and wheat is low. The anilide compounds (I) exhibit a strong control not only against those weeds but also against redroot pigweed (*Amaranthus retroflexus*), common lambsquarters (*Chenopodium album*), wild mustard (*Brassica arvensis*), black bindweed (*Polygonum convolvulus*), black nightshade (*Solanum nigrum*), etc.

As stated above, the anilide compounds (I) having a methyl group at the 1-position on the cyclopropane ring are particularly advantageous in that the toxicity against wheat is much reduced. For instance, N'-3-[2-(2,2-dichlorocyclopropyl)ethoxy]phenyl-N-methoxy-N-methylurea (Compound No. 1) produces a material toxicity against wheat at a dose of 10 grams per are, while the corresponding methylated compound, i.e. N'-3-[2-(1-methyl-2,2-dichlorocyclopropyl)ethoxy]phenyl-N-methoxy-N-methylurea (Compound No. 2), as well as its bromo analogue, i.e. N'-3-[2-(1-methyl-2,2-dibromocyclopropyl)ethoxy]phenyl-N-methoxy-N-methylurea (Compound No. 5), do not produce any material toxicity at the same dose as above.

From the above comparisons, it may be understood that the herbicidal activity could be much enhanced by extending one methylene chain from the cyclopropylmethoxy group of the control (a), and further the selectivity to wheat could be much improved by introducing a methyl group into the 1-position of the cyclopropane ring. These enhancement and improvement are entirely of unexpected nature.

Still, the anilide compounds (I) include some other compounds, such as N-3-[2-(1-methyl-2,2-dichlorocyclopropyl)ethoxy]propionanilide (Compound No. 15), which can be safely used in the field of wheat. Still-more, the anilide compounds (I) include some other compounds having a high selectivity to soybean by foliar treatment after emergence. For instance, N'-4-[2-(2,2-dichlorocyclopropyl)ethoxy]phenyl-N-methoxy-N-methylurea (Compound No. 13) can be safely used in the field of soybean.

Accordingly, the anilide compounds (I) are useful as the selective herbicides applicable to the agricultural land. They are also useful as the herbicides to be employed for non-agricultural land due to their strong herbicidal potency.

The anilide compound (I) can be produced by reacting an aniline compound of the formula:

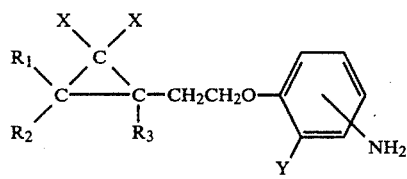
(II)

wherein $R_1$, $R_2$, $R_3$, X and Y are each as defined above with an acyl chloride of the formula:

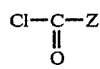

wherein Z is as defined above.

The reaction may be carried out in an organic solvent (e.g. benzene, toluene, xylene, diethyl ether, tetrahydrofuran, dioxane, chloroform, carbon tetrachloride, ethyl acetate, pyridine, dimethylformamide). The presence of a hydrogen chloride-eliminating agent in the reaction system is favorable for obtaining the desired product in a better yield. Examples of such hydrogen chloride-eliminating agent includes pyridine, triethylamine, sodium hydroxide, potassium hydroxide, etc. The reaction is effected, for instance, from 0° to 150° C. usually within the period of time up to 10 hours.

The aniline compound (II), which is used as the starting material in the said process, can be obtained by reduction of the corresponding nitrobenzene compound of the formula:

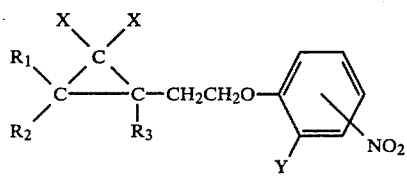
(III)

wherein $R_1$, $R_2$, $R_3$, X and Y are each as defined above.

The reduction may be accomplished by any per se conventional procedure such as catalytic reduction using platinum oxide or reduction with a hydrazine compound. For instance, in case of the catalytic reduction using platinum oxide, it may be effected by treatment with hydrogen in an organic solvent (e.g. benzene, toluene, ethanol, methanol, isopropanol, tetrahydrofuran, dioxane) at a temperature of 0° to 100° C. under atmospheric or elevated pressure for a period of 30 minutes to 10 hours.

The said nitrobenzene compound (III) is obtainable from the corresponding known nitrobenzene compound of the formula:

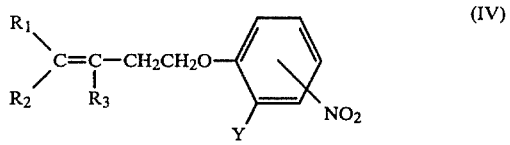
(IV)

wherein $R_1$, $R_2$, $R_3$ and Y are each as defined above [D. H. Rammler et al.: Analytical Biochemistry, 52, 180 (1973)] by reacting the latter with dichlorocarbene or dibromocarbene in a per se conventional procedure [Japanese Patent Publn. (unexamined) No. 117440/1979].

The reaction may be carried out in a mixture of a haloform (e.g. chloroform, bromoform) and an aqueous alkali metal solution such as an aqueous sodium hydroxide solution in the presence of a phase transfer catalyst (e.g. quaternary ammonium salt) at a temperature of 0° to 100° C. for a period of 30 minutes to 10 hours.

Specific examples of the anilide compound (I) are shown below:

| Compound No. | Structure | Physical property |
|---|---|---|
| 1 | Cl₂C(CH₂—CHCH₂CH₂O—C₆H₄—NHC(O)N(CH₃)(OCH₃)) (cyclopropane) | M.P., 75–76° C. |
| 2 | Cl₂C(CH₂—C(CH₃)CH₂CH₂O—C₆H₄—NHC(O)N(CH₃)(OCH₃)) (cyclopropane) | M.P., 91–92° C. |
| 3 | Cl₂C(CH₂—C(CH₃)CH₂CH₂O—C₆H₄—NHC(O)N(CH₃)(CH₃)) (cyclopropane) | M.P., 111–112° C. |
| 4 | (H₃C)₂C—C(Cl₂)—CHCH₂CH₂O—C₆H₄—NHC(O)N(CH₃)(CH₃) (cyclopropane) | M.P., 112–114° C. |
| 5 | Br₂C(CH₂—C(CH₃)CH₂CH₂O—C₆H₄—NHC(O)N(OCH₃)(CH₃)) (cyclopropane) | M.P., 86–87.5° C. |

-continued

| Compound No. | Structure | Physical property |
|---|---|---|
| 6 | Br,Br-C-CH₂-C(CH₃)CH₂CH₂O-C₆H₄-NHC(O)N(CH₃)CH₃ | M.P., 100–101° C. |
| 7 | Cl,Cl-C-CH₂-C(CH₃)CH₂CH₂O-C₆H₃(Cl)-NHC(O)N(OCH₃)CH₃ | $n_D^{22}$ 1.5503 |
| 8 | Cl,Cl-C-CH₂-C(CH₃)CH₂CH₂O-C₆H₃(Cl)-NHC(O)N(CH₃)CH₃ | M.P., 92–93.5° C. |
| 9 | Cl,Cl-C-CH₂-C(CH₃)CH₂CH₂O-C₆H₄-NHC(O)N(OCH₃)CH₃ | $n_D^{21}$ 1.5480 |
| 10 | Cl,Cl-C-CH₂-C(CH₃)CH₂CH₂O-C₆H₄-NHC(O)N(CH₃)CH₃ | M.P., 106–107° C. |
| 11 | Cl,Cl-C-CH₂-CHCH₂CH₂O-C₆H₄-NHC(O)N(CH₃)CH₃ | M.P., 123–124.5° C. |
| 12 | (H₃C)₂C(Cl,Cl)-C-CHCH₂CH₂O-C₆H₄-NHC(O)N(OCH₃)CH₃ | M.P., 78–79° C. |
| 13 | Cl,Cl-C-CH₂-CHCH₂CH₂O-C₆H₄-NHC(O)N(OCH₃)CH₃ | $n_D^{23}$ 1.5431 |
| 14 | Cl,Cl-C-CH₂-CHCH₂CH₂O-C₆H₄-NHC(O)N(CH₃)CH₃ | M.P., 103–104.5° C. |
| 15 | Cl,Cl-C-CH₂-C(CH₃)CH₂CH₂O-C₆H₄-NHC(O)C₂H₅ | M.P., 77–78° C. |
| 16 | Br,Br-C-CH₂-C(CH₃)CH₂CH₂O-C₆H₄-NHC(O)C₂H₅ | $n_D^{25}$ 1.5545 |
| 17 | Cl,Cl-C-CH₂-C(CH₃)CH₂CH₂O-C₆H₃(Cl)-NHC(O)C₂H₅ | M.P., 93–94° C. |
| 18 | Cl,Cl-C-CH₂-C(CH₃)CH₂CH₂O-C₆H₃(Cl)-NHC(O)-cyclopropyl | M.P., 87–89° C. |
| 19 | Cl,Cl-C-CH₂-CHCH₂CH₂O-C₆H₄-NHC(O)C₂H₅ | M.P., 68–69° C. |
| 20 | Cl,Cl-C-CH₂-CHCH₂CH₂O-C₆H₄-NHC(O)C₂H₅ | $n_D^{22.5}$ 1.5492 |

Some practical embodiments of the process for preparing the anilide compound (I) are illustratively shown below.

EXAMPLE 1

Synthesis of N'-3-[2-(1-methyl-2,2-dichlorocyclopropyl)ethoxy]phenyl-N-methoxy-N-methylurea:

To a solution of 3-[2-(1-methyl-2,2-dichlorocyclopropyl)ethoxy]aniline (12 g) in 100 ml of pyridine was added 6 g of N-methoxy-N-methylcarbamyl chloride. After allowed to stand at room temperature overnight, the resultant mixture was poured into a mixture of dilute hydrochloric acid and ice-water, followed by extraction with ethyl acetate. The organic layer was washed with a saturated solution of sodium bicarbonate and dried over anhydrous sodium sulfate. The solvent was removed under reduced pressure, and the residue was recrystallized from ethanol to give 13.8 g of N'-3-[2-(1-methyl-2,2-dichlorocyclopropyl)ethoxy]phenyl-N-methoxyurea (Compound No. 2).

M.P., 91°–92° C.

Elementary analysis: Calcd. for $C_{15}H_{20}O_3N_2Cl_2$: C, 51.88%; H, 5.81%; N, 8.07%; Cl, 20.42%. Found: C, 52.05%; H, 5.95%; N, 8.16%; Cl, 20.43%.

EXAMPLE 2

Synthesis of N'-3-chloro-4-[2-(1-methyl-2,2-dichlorocyclopropyl)ethoxy]phenyl-N,N-dimethylurea:

To a solution of 3-chloro-4-[2-(1-methyl-2,2-dichlorocyclopropyl)ethoxy]aniline (3 g) in 50 ml of pyridine was added 1.1 g of N,N-dimethylcarbamyl chloride. After stirring at room temperature for 2 hours, the resultant mixture was poured into a mixture of dilute hydrochloric acid and ice-water, followed by extraction with ethyl acetate. The solvent was removed under reduced pressure, and the residue was recrystallized from ethanol to give 3.3 g of N'-3-chloro-4-[2-(1-methyl-2,2-dichlorocyclopropyl)ethoxy]phenyl-N,N-dimethylurea (Compound No. 8). M.P., 92°–93.5° C.

Elementary analysis: Calcd. for $C_{15}H_{19}O_2N_2Cl_3$: C, 49.26%; H, 5.24%; N, 7.66%; Cl, 29.09%. Found: C, 49.30%; H, 5.19%; N, 7.61%; Cl, 29.08%.

EXAMPLE 3

Synthesis of N'-3-[2-(1-methyl-2,2-dibromocyclopropyl)ethoxy]phenyl-N-methoxy-N-methylurea:

To a solution of 3-[2-(1-methyl-2,2-dibromocyclopropyl)ethoxy]aniline (6 g) in 50 ml of pyridine was added 2.4 g of N-methoxy-N-methylcarbamyl chloride. After allowed to stand at room temperature for 2 hours, the resultant mixture was poured into a mixture of dilute hydrochloric acid and ice-water, followed by extraction with ethyl acetate. The extract was concentrated under reduced pressure, and the residue was recrystallized from ethanol to give 6.9 g of N'-3-[2-(1-methyl-2,2-dibromocyclopropyl)ethoxy]phenyl-N-methoxy-N-methylurea (Compound No. 5). M.P., 66°–67.5° C.

Elementary analysis: Calcd. for $C_{15}H_{20}O_3N_2Br_2$: C, 41.30%; H, 4.62%; N, 6.42%; Br, 36.64%. Found: C, 41.33%; H, 4.65%; N, 6.40%; Br, 36.69%.

EXAMPLE 4

Synthesis of N-3-[2-(1-methyl-2,2-dichlorocyclopropyl)ethoxy]propionanilide:

To a solution of 3-[2-(1-methyl-2,2-dichlorocyclopropyl)ethoxy]aniline (12 g) in 100 ml of pyridine was added 4.3 g of propionyl chloride. After allowed to stand at room temperature overnight, the resultant mixture was poured into a mixture of dilute hydrochloric acid and ice-water, followed by extraction with ethyl acetate. The solvent was removed under reduced pressure and recrystallized from ethanol to give 13.3 g of N-3-[2-(1-methyl-2,2-dichlorocyclopropyl)ethoxy]propionanilide (Compound No. 15). M.P., 77°–78° C.

Elementary analysis: Calcd. for $C_{15}H_{19}O_2NCl_2$: C, 56.97%; H, 6.06%; N, 4.43%; Cl, 22.42%. Found: C, 57.16%; H, 6.20%; N, 4.53%; Cl, 22.44%.

Some practical embodiments of the production of the starting materials are shown below.

EXAMPLE 5

Synthesis of 3-chloro-4-[2-(1-methyl-2,2-dichlorocyclopropyl)ethoxy]aniline:

A suspension of 12 g of 3-chloro-4-[2-(1-methyl-2,2-dichlorocyclopropyl)ethoxy]nitrobenzene and 0.1 g of platinum dioxide in benzene-ethanol (1:1) was subjected to catalytic reduction under room temperature and atmospheric pressure, whereby 2.5 liters of hydrogen were absorbed. The resulting mixture was filtered, and the solvent was removed under reduced pressure. The residue was recrystallized from ethanol to give 10 g of 3-chloro-4-[2-(1-methyl-2,2-dichlorocyclopropyl)ethoxy]aniline.

M.P., 73°–74.5° C.

Elementary analysis: Calcd. for $C_{12}H_{14}ONCl_3$: C, 48.92%; H, 4.79%; N, 4.75%; Cl, 36.11%. Found: C, 49.97%; H, 4.76%; N, 4.72%; Cl, 36.09%.

In the same manner as in Example 5, the following aniline compounds (II) were produced:

| Structure | Physical property |
|---|---|
| Cl₂C(cyclopropyl)—CH₂—C(CH₃)(CH₂CH₂O—C₆H₄—NH₂) [2,6-disubst. / ortho-NH₂] | $n_D^{25}$ 1.5623 |
| Cl₂C(cyclopropyl)—CH₂—C(CH₃)(CH₂CH₂O—C₆H₄—NH₂) [para-NH₂] | $n_D^{25}$ 1.5605 |
| Br₂C(cyclopropyl)—CH₂—C(CH₃)(CH₂CH₂O—C₆H₄—NH₂) | $n_D^{25}$ 1.5120 |

EXAMPLE 6

Synthesis of 3-chloro-4-[2-(1-methyl-2,2-dichlorocyclopropyl)ethoxy]nitrobenzene:

Into a solution of 17 g of 3-chloro-4-(3-methyl-3-butenyloxy)nitrobenzene and 0.4 g of tetra-n-butylammonium bromide in chloroform (29.4 g), a 50% sodium hydroxide solution (78.2 g) was dropwise added while stirring at room temperature, and stirring was continued at 50° C. for 2.5 hours. The resultant mixture was poured into ice-water and extracted with chloroform. The extract was concentrated under reduced pressure, and the precipitated crystals were subjected to filtration by a glass filter and washed with ether to give 19.4 g of 3-chloro-4-[2-(1-methyl-2,2-dichlorocyclopropyl)ethoxy]nitrobenzene.

M.P., 69°–70° C.

Elementary analysis: Calcd. for $C_{12}H_{12}O_3NCl_3$: C, 44.40%; H, 3.73%; N, 4.32%; Cl, 32.77%. Found: C, 44.40%; H, 3.66%; N, 4.36%, Cl, 32.65%.

In the same manner as in Example 6, the following nitrobenzene compounds (III) were produced:

| Structure | Physical property |
|---|---|
| Cl₂C(cyclopropyl)—CH₂—C(CH₃)(CH₂CH₂O—C₆H₄—NO₂) | $n_D^{25}$ 1.5525 |

| Structure | Physical property |
|---|---|
| -continued Br Br \ / C / \ CH₂—CCH₂CH₂O—⟨phenyl with NO₂⟩ \| CH₃ | $n_D^{25}$ 1.5830 |

REFERENCE EXAMPLE 1

Synthesis of 3-chloro-4-(3-methyl-3-butenyloxy)nitrobenzene:

3-Methyl-3-butenyltosylate derived from 12.9 g of 3-methyl-3-buten-1-ol by a conventional procedure was reacted with 31 g of sodium salt of 2-chloro-4-nitrophenol in 250 ml of dimethylformamide. The resultant mixture was stirred at 90°-100° C. for 2.5 hours and then poured into ice-water, followed by extraction with benzene. The solvent was removed under reduced pressure, and the precipitated crystals were subjected to filtration by a glass filter and washed with ether to give 29.3 g of 3-chloro-4-(3-methyl-3-butenyloxy)nitrobenzene. M.P. 38°-39° C.

Elementary analysis: Calcd. for $C_{11}H_{12}O_3NCl$: C, 54.66%; H, 5.01%; N, 5.80%; Cl, 14.67%. Found: C, 54.62%; H, 5.05%; N, 5.83%; Cl, 14.69%.

In the practical usage of the anilide compounds (I), they may be applied as such or in any preparation form such as wettable powders, emulsifiable concentrates, granules, fine granules, dusts or suspensions.

For production of said preparation forms, solid or liquid carriers or diluents may be used. As for the solid carrier or diluent, there may be exemplified mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be exemplified alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. If necessary, gelatin, casein, sodium alginate, starch, agar, polyvinyl alcohol or the like may be used as an auxiliary agent.

In the herbicidal composition of this invention, the content of the anilide compounds (I) may be usually from 1 to 95% by weight, preferably from 1 to 80% by weight.

Practical embodiments of the herbicidal composition according to the invention are illustratively shown in the following examples wherein part(s) and % are by weight.

PREPARATION EXAMPLE 1

Eighty parts of Compound No. 1, 5 parts of polyoxyethylene alkylaryl ether and 15 parts of synthetic silica hydrate are well mixed while being powdered to obtain a wettable powder preparation.

PREPARATION EXAMPLE 2

Thirty parts of Compound No. 2, 7 parts of polyoxyethylene alkylaryl ether, 3 parts of alkylaryl sulfonate and 60 parts of xylene are well mixed to obtain an emulsifiable concentrate preparation.

PREPARATION EXAMPLE 3

One part of Compound No. 4, 1 part of white carbon, 5 parts of ligninsulfonate and 93 parts of clay are well mixed while being powdered. The mixture is then well kneaded with water, granulated and dried to obtain a granule preparation.

PREPARATION EXAMPLE 4

Fourty parts of bentonite, 5 parts of ligninsulfonate and 55 parts of clay are well mixed while being powdered. The mixture is then well kneaded with water, granulated and dried to obtain a granule containing no active ingredient. The granule is then impregnated with 5 parts of Compound No. 5 to obtain a granule preparation.

PREPARATION EXAMPLE 5

Three parts of Compound No. 6, 0.5 part of isopropyl phosphate, 66.5 parts of clay and 30 parts of talc are well mixed while being powdered to obtain a dust preparation.

PREPARATION EXAMPLE 6

Twenty parts of Compound No. 8 is mixed with 60 parts of an aqueous solution containing 3% polyoxyethylene sorbitan monolactate and grained until the particle size of the active ingredient becomes less than 3 microns. Twenty parts of an aqueous solution containing 3% of sodium alginate as a dispersing agent is introduced therein to obtain a suspension preparation.

The anilide compounds (I) may be used together with other herbicides and/or fungicides to improve their activity as herbicides, and in some cases, to produce a synergistic effect. As the other herbicides or fungicides, there may be given 2,4-dichlorophenoxyacetic acid, sodium 5-[2-chloro-4-(trifluoromethyl)phenoxy]-2-nitrobenzoate, 2-chloro-4-ethylamino-6-isopropyl, amino S-triazine, 2-methylthio-4,6-bis(isopropylamino)-S-triazine, 3-(3,4-dichlorophenyl)-1,1-dimethylurea, 3-(α,α,α-trifluoro-m-tolyl)-1,1-dimethylurea, isopropyl-N-(3-chlorophenyl)carbamate, 3,4-dichloropropyonanilide, 3-cyclohexyl-5,6-trimethyluracil, O-methyl-O-(2-nitro-5-methylphenyl)-N-sec-butylphosphoroamidothioate, 3-isopropyl-1H-2,1,3-benzothiadiazine(4)-3H-one-2,2-dioxide, disodium methanearsonate, N-(3,5- dichlorophenyl)-1,2-dimethylcyclopropane-1,2-dicarboximide, S-n-butyl-S-p-tert-butylbenzyl-N-3-pyridylcarbonimidate, O,O-dimethyl-O-2,6-dichloro-4-methylphenylphosphorothioate, methyl-N-benzimidazol-2-yl-N-(butylcarbamoyl)carbamate, N-trichloromethylthio-4-cyclohexene-1,2-dicarboximide, cis-N-(1,1,2,2-tetrachloroethylthio)-4-cyclohexene-1,2-dicarboximide, polyoxin, streptomycin, zinc ethylenebisdithiocarbamate, zinc dimethylthiocarbamate, manganese ethylenebisdithiocarbamate, bis(dimethylthiocarbamoyl)disulfide, tetrachloroisophthanonitrile, 8-hydroxyquinone, dodecylguanidine acetate, 5,6-dihydro-2-methyl-1,4-oxathiin-3-carboxanilide, N'-dichlorofluromethylthio-N,N-dimethyl-N'-phenylsulfamide, 1-(4-chlorophenoxy)-3,3-dimethyl-1-(1,2,4-triazol-1-yl)-2-butane, 1,2-bis(3-methoxycarbonyl-2-thioureido)benzene and the like. However, the herbicides and/or fungicides are not of course limited to these examples.

Also, the anilide compounds (I) may be applied together with microbicidal agricultural chemicals, organic phosphorus series insecticides, carbamate series insecticides, pyrethroid series insecticides, other insecticides, plant growth regulators, fertilizers, etc.

The dosage of the anilide compounds (I) depends upon their kinds, the sorts of cultivated plants, the method of application, weather, etc. Generally, however, the dosage is from 1 to 200 grams, preferably from 2 to 50 grams, of the active ingredient per are.

The application of the anilide compounds (I) as herbicides will be illustratively shown in the following Examples wherein the phytotoxicity to cultivated plants and the herbicidal activity on weeds were evaluated as follows: the aereal parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and to control weeds, respectively. The rating values in the paddy rice test alone were calculated from the dry weight of the plant.

| Rating value | Fresh weight (percentage to untreated plot) | |
|---|---|---|
| | Cultivated plant | Weed |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples.

Control (a)

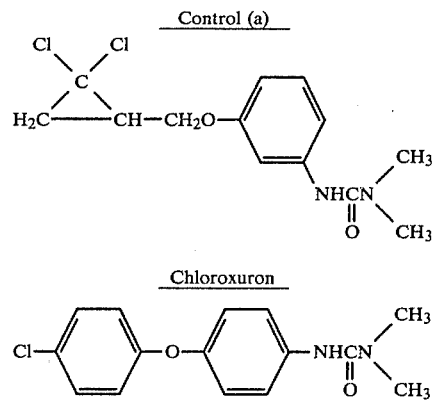

Chloroxuron

EXAMPLE I (1) Post-emergence treatment:

Plastic pots (each 500 ml volume) were filled with upland field soil, and the seeds of barnyard grass, wild oat, raddish and velvetleaf were separately sowed in the pots and grown for 2 weeks in a greenhouse. The designed amount of the test compound each formulated into an emulsifiable concentrate was sprayed to the foliage of the plants over the top by means of a small hand sprayer. After the spraying, the test plants were grown for further 3 weeks in the greenhouse, and the herbicidal activity was examined. The results are shown in Table 1. In this treatment, the emulsifiable concentrate was dispersed in water for application at a spray volume of 5 liters per are and applied with the addition of a wetting agent.

(2) Paddy field treatment:

Plastic pots (each 500 ml volume) were filled with paddy field soil containing seeds of weeds and, water was poured therein until the depth of water became 4 cm. Rice seedlings of 2-leaf grown stage, buds of slender spikerush, which tided over the winter, and tubers of arrowhead (Sagitlaria pygmoea) were transplanted into the pots and grown for 4 days in the greenhouse. The designed amount of the test compound each formulated into an emulsifiable concentrate was applied to the pots by a perfusion. Three weeks after the application, the herbicidal activity and phytotoxicity were checked on the plants as well as the weeds such as barnyard grass and broad-leaved weeds (e.g. pickerel weed, false pimpernel, toothcup). The results are also shown in Table 1. In this treatment, the emulsifiable concentrate was dispersed in water for application at a perfusion volume of of 10 liters per are to the pots.

TABLE 1

| Compound No. | Dosage of active ingredient (g/are) | Post-emergence treatment Herbicidal activity | | | | Paddy field treatment Herbicidal activity | | | | Phytotoxicity |
|---|---|---|---|---|---|---|---|---|---|---|
| | | Barnyardgrass | Wild oat | Raddish | Velvetleaf | Barnyardgrass | Broad-leaved weeds | Slender spikerush | Arrowhead | Rice plant |
| 1 | 40 | 5 | 5 | 5 | 5 | 5 | 5 | 5 | 5 | 2 |
|   | 20 | 5 | 5 | 5 | 5 | 5 | 5 | 5 | 3 | 1 |
| 2 | 40 | 5 | 5 | 5 | 5 | 4 | 5 | 4 | 5 | 2 |
|   | 20 | 5 | 5 | 5 | 5 | 4 | 5 | 3 | 5 | 1 |
| 3 | 40 | 5 | 5 | 5 | 5 | 5 | 5 | 4 | 3 | 1 |
|   | 20 | 5 | 5 | 5 | 5 | 5 | 5 | 3 | 2 | 0 |
| 4 | 40 | 5 | 5 | 5 | 5 | — | — | — | — | — |
|   | 20 | 5 | 5 | 5 | 5 | — | — | — | — | — |

TABLE 1-continued

| Compound No. | Dosage of active ingredient (g/are) | Post-emergence treatment Herbicidal activity | | | | Paddy field treatment Herbicidal activity | | | | Phytotoxicity |
|---|---|---|---|---|---|---|---|---|---|---|
| | | Barnyard-grass | Wild oat | Raddish | Velvet-leaf | Barnyard-grass | Broad-leaved weeds | Slender spikerush | Arrowhead | Rice plant |
| 5 | 40 | 5 | 5 | 5 | 5 | 5 | 5 | 4 | 5 | 1 |
|  | 20 | 5 | 5 | 5 | 5 | 5 | 5 | 3 | 4 | 0 |
| 6 | 40 | 5 | 5 | 5 | 5 | 4 | 5 | 4 | 4 | 1 |
|  | 20 | 5 | 5 | 5 | 5 | 3 | 5 | 3 | 3 | 0 |
| 7 | 40 | 5 | 5 | 5 | 5 | 5 | 5 | 4 | 5 | 3 |
|  | 20 | 5 | 5 | 5 | 5 | 4 | 5 | 3 | 4 | 1 |
| 8 | 40 | 5 | 5 | 5 | 5 | 4 | 5 | 4 | 4 | 1 |
|  | 20 | 5 | 5 | 5 | 5 | 3 | 5 | 3 | 3 | 1 |
| 9 | 40 | 5 | 5 | 5 | 5 | 4 | 5 | 4 | 4 | 2 |
|  | 20 | 5 | 5 | 5 | 5 | 3 | 5 | 3 | 4 | 1 |
| 10 | 40 | 5 | 5 | 5 | 5 | 4 | 5 | 4 | 3 | 1 |
|  | 20 | 5 | 5 | 5 | 5 | 3 | 5 | 3 | 2 | 0 |
| 11 | 40 | 5 | 5 | 5 | 5 | 5 | 5 | 5 | 5 | 1 |
|  | 20 | 5 | 5 | 5 | 5 | 5 | 5 | 5 | 5 | 0 |
| 12 | 40 | 5 | 5 | 5 | 5 | 5 | 5 | 4 | 5 | 0 |
|  | 20 | 5 | 5 | 5 | 5 | 3 | 5 | 3 | 4 | 0 |
| 13 | 40 | 5 | 5 | 5 | 5 | 5 | 5 | 5 | 5 | 0 |
|  | 20 | 5 | 5 | 5 | 5 | 4 | 5 | 4 | 5 | 0 |
| 14 | 40 | 5 | 5 | 5 | 5 | 5 | 5 | 5 | 5 | 1 |
|  | 20 | 5 | 5 | 5 | 5 | 5 | 5 | 4 | 4 | 0 |
| 15 | 40 | 5 | 5 | 5 | 5 | 1 | 5 | 4 | 3 | 0 |
|  | 20 | 5 | 5 | 5 | 5 | 1 | 5 | 3 | 2 | 0 |
| 16 | 40 | 5 | 5 | 5 | 5 | 2 | 5 | 3 | 2 | 0 |
|  | 20 | 5 | 5 | 5 | 5 | 1 | 5 | 2 | 2 | 0 |
| 17 | 40 | 5 | 5 | 5 | 5 | 3 | 5 | 2 | 4 | 0 |
|  | 20 | 5 | 4 | 5 | 5 | 2 | 5 | 2 | 2 | 0 |
| 18 | 40 | 5 | 5 | 5 | 5 | 3 | 5 | 3 | 3 | 0 |
|  | 20 | 4 | 3 | 5 | 5 | 2 | 5 | 2 | 2 | 0 |
| 19 | 40 | 5 | 4 | 5 | 5 | 1 | 5 | 0 | 1 | 0 |
|  | 20 | 4 | 3 | 5 | 5 | — | — | — | — | — |
| 20 | 40 | 5 | 5 | 5 | 5 | 3 | 5 | 5 | 0 | 0 |
|  | 20 | 4 | 3 | 5 | 5 | 2 | 5 | 3 | 0 | 0 |
| Control (a) | 40 | 5 | 5 | 5 | 5 | 3 | 5 | 3 | 3 | 4 |
|  | 20 | 4 | 3 | 5 | 5 | 2 | 5 | 3 | 3 | 2 |

EXAMPLE II

Post-emergence foliar treatment on wheat:

Plastic trays (35 cm×25 cm×10 cm) were filled with upland field soil, and the seeds of redroot pigweed, common lambsquarters, *Brassica arvensis*, common chickweed, black bindweed, catchweed bedstraw, black nightshade, wild oat and barnyard grass and the seeds of wheat were separately sowed in the trays and grown for 3 weeks in a greenhouse. The designed amount of the test compound each formulated into an emulsifiable concentrate was sprayed to the whole foliage part of the test plants over the top by means of a small hand sprayer. After the spraying, the test plants were grown for further 3 weeks in the greenhouse, and the herbicidal activity and phytotoxicity were examined. The results are shown in Table 2. In this treatment, the emulsifiable concentrate was dispersed in water for application at a spray volume of 5 liters per are and applied with the addition of a wetting agent.

The growing stage of the test plants varied on their kind. However, the weeds were generally at 2 to 4 leaf stage and in 2 to 12 cm heights, and the wheat was at 2 to 3 leaf stage and in 15 to 20 cm heights.

TABLE 2

| Compound No. | Dosage of active ingredient (g/are) | Herbicidal activity | | | | | | | | | Phytotoxicity Wheat |
|---|---|---|---|---|---|---|---|---|---|---|---|
| | | Redroot pigweed | Common lambs-quarters | Brassica arvensis | Common chick-weed | Black bind-weed | Catchweed bedstraw | Black night-shade | Wild oat | Barnyard grass | |
| 1 | 10 | 5 | 5 | 5 | 5 | 5 | 5 | 5 | 5 | 4 | 2 |
|  | 5 | 5 | 5 | 5 | 5 | 5 | 5 | 5 | 4 | 3 | 1 |
|  | 2.5 | 5 | 5 | 5 | 5 | 5 | 5 | 5 | 3 | 3 | 0 |
| 2 | 10 | 5 | 5 | 5 | 5 | 5 | 5 | 5 | 4 | 3 | 0 |
|  | 5 | 5 | 5 | 5 | 5 | 5 | 5 | 5 | 4 | 2 | 0 |
| 3 | 10 | 5 | 5 | 5 | 5 | 5 | 5 | 5 | 3 | 3 | 0 |
|  | 5 | 5 | 5 | 5 | 5 | 5 | 5 | 5 | 2 | 1 | 0 |
| 4 | 10 | 5 | 5 | 5 | 5 | 5 | 5 | 5 | 3 | 4 | 1 |
|  | 5 | 5 | 5 | 5 | 5 | 5 | 4 | 5 | 2 | 3 | 0 |
| 5 | 10 | 5 | 5 | 5 | 5 | 5 | 5 | 5 | 4 | 4 | 0 |
|  | 5 | 5 | 5 | 5 | 5 | 5 | 5 | 5 | 3 | 2 | 0 |
| 6 | 10 | 5 | 5 | 5 | 5 | 5 | 5 | 5 | 4 | 3 | 1 |
|  | 5 | 5 | 5 | 5 | 5 | 5 | 5 | 5 | 3 | 2 | 0 |
| 7 | 10 | 5 | 5 | 5 | 5 | 5 | 5 | 5 | 4 | 4 | 0 |
|  | 5 | 5 | 5 | 5 | 5 | 5 | 5 | 5 | 3 | 3 | 0 |
| 8 | 10 | 5 | 5 | 5 | 5 | 5 | 5 | 5 | 3 | 3 | 0 |
|  | 5 | 5 | 5 | 5 | 5 | 5 | 5 | 5 | 2 | 2 | 0 |
| 9 | 10 | 5 | 5 | 5 | 5 | 5 | 5 | 5 | 4 | 4 | 1 |
|  | 5 | 5 | 5 | 5 | 5 | 5 | 5 | 5 | 3 | 2 | 0 |
| 10 | 10 | 5 | 5 | 5 | 5 | 5 | 5 | 5 | 3 | 2 | 0 |

TABLE 2-continued

| Compound No. | Dosage of active ingredient (g/are) | Redroot pigweed | Common lambsquarters | Brassica arvensis | Common chickweed | Black bindweed | Catchweed bedstraw | Black nightshade | Wild oat | Barnyard grass | Phytotoxicity Wheat |
|---|---|---|---|---|---|---|---|---|---|---|---|
| 11 | 5 | 5 | 5 | 5 | 5 | 5 | 5 | 5 | 2 | 2 | 0 |
| 11 | 10 | 5 | 5 | 5 | 5 | 5 | 5 | 5 | 4 | 4 | 1 |
| 13 | 5 | 5 | 5 | 5 | 5 | 5 | 5 | 5 | 3 | 2 | 0 |
| 13 | 10 | 5 | 5 | 5 | 5 | 5 | 5 | 5 | 4 | 4 | 1 |
| 14 | 5 | 5 | 5 | 5 | 5 | 5 | 5 | 5 | 3 | 3 | 1 |
| 14 | 10 | 5 | 5 | 5 | 5 | 5 | 5 | 5 | 3 | 4 | 1 |
| 15 | 5 | 5 | 5 | 5 | 5 | 5 | 5 | 5 | 2 | 3 | 0 |
| 15 | 20 | 5 | 5 | 5 | 5 | 5 | 5 | 5 | 5 | 5 | 0 |
| 16 | 5 | 5 | 5 | 5 | 5 | 5 | 5 | 5 | 4 | 4 | 0 |
| 16 | 20 | 5 | 5 | 5 | 5 | 5 | 5 | 5 | 4 | 3 | 0 |
| 17 | 10 | 5 | 5 | 5 | 4 | 5 | 4 | 4 | 3 | 2 | 0 |
| 17 | 20 | 5 | 5 | 5 | 5 | 5 | 5 | 5 | 2 | 3 | 0 |
| 20 | 10 | 5 | 5 | 5 | 5 | 5 | 4 | 3 | 0 | 2 | 0 |
| 20 | 20 | 5 | 5 | 5 | 5 | 5 | 5 | 5 | 4 | 2 | 1 |
| Control (a) | 10 | 5 | 5 | 5 | 3 | 4 | 2 | 4 | 1 | 0 | 1 |
| Control (a) | 5 | 5 | 5 | 4 | 2 | 3 | 1 | 3 | 0 | 0 | 0 |

EXAMPLE III

Post-emergence foliar treatment on soybean:

Plastic trays (35 cm×25 cm×10 cm) were filled with upland field soil, and the seeds of redroot pigweed, common lambsquarters, common morningglory, cocklebur (*Xanthium pennsylvanicum*), Sesbania spp., velvetleaf, green foxtail (*Setaria viridis*) and large crabgrass (*Digitaria sanguinalis*) and the seeds of soybean were separately sowed in the trays and grown for 19 days in a greenhouse. The designed amount of the test compound each formulated into an emulsifiable concentrate was sprayed to the whole foliage part of the test plants over the top by means of a small hand sprayer. After the spraying, the test plants were grown for further 18 days in the greenhouse, and the herbicidal activity and phytotoxicity were examined. The results are shown in Table 3. In this treatment, the emulsifiable concentrate was dispersed in water for application at a spray volume of 5 liters per are and applied with the addition of a wetting agent.

The growing stage of the test plants varied on their kind. However, the weeds were generally at 2 to 4 leaf stage and in 4 to 20 cm heights and the soybean was at trifoliage stage and in 20 cm heights.

What is claimed is:

1. A compound of the formula:

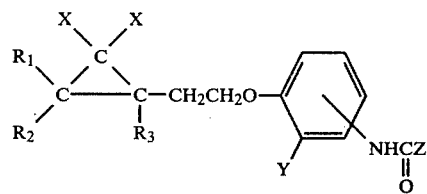

wherein $R_1$, $R_2$ and $R_3$, which may be same or different, are each hydrogen or $C_1$–$C_4$ alkyl, X is chlorine or bromine, Y is hydrogen, chlorine, bromine, fluorine or iodine and Z is N-methoxy-N-methylamino.

2. The compound according to claim 1, wherein $R_1$, $R_2$ and $R_3$ are each hydrogen or methyl, Y is hydrogen or chlorine and Z is N-methoxy-N-methylamino.

3. N'-3-[2-(1-Methyl-2,2-dichlorocyclopropyl)ethoxy]phenyl-N-methoxy-N-methylurea.

4. N'-3-[2-(1-Methyl-2,2-dibromocyclopropyl)ethoxy]phenyl-N-methoxy-N-methylurea.

5. N'-4-[2-(2,2-Dichlorocyclopropyl)ethoxy]phenyl-N-methoxy-N-methylurea.

* * * * *

TABLE 3

| Compound No. | Dosage of active ingredient (g/are) | Redroot pigwood | Common lambsquarters | Common morningglory | Cocklebur | Sesbania spp. | Velvetleaf | Green foxtail | Large crabgrass | Phytotoxicity Soybean |
|---|---|---|---|---|---|---|---|---|---|---|
| 13 | 10 | 5 | 5 | 5 | 5 | 5 | 5 | 5 | 4 | 1 |
| 13 | 5 | 5 | 5 | 5 | 5 | 5 | 5 | 4 | 3 | 0 |
| Chloroxuron | 10 | 5 | 5 | 5 | 5 | 5 | 4 | 3 | 3 | 2 |
| Chloroxuron | 5 | 5 | 5 | 4 | 4 | 4 | 2 | 2 | 2 | 1 |